United States Patent [19]

Marten

[11] Patent Number: 4,795,465
[45] Date of Patent: Jan. 3, 1989

[54] TRACHEOBRONCHIAL STENT
[75] Inventor: Lewis H. Marten, Quincy, Mass.
[73] Assignee: Hood Laboratories, Pembroke, Mass.
[21] Appl. No.: 49,399
[22] Filed: May 14, 1987
[51] Int. Cl.[4] .............................................. A61F 2/04
[52] U.S. Cl. ............................................ 623/9; 623/12
[58] Field of Search .......................... 623/1, 9, 11, 12; 128/334 R, 334 C, 1 R

[56]  References Cited
U.S. PATENT DOCUMENTS

| 909,002 | 1/1909 | Lambert | 128/207.14 |
| 3,721,233 | 3/1973 | Montgomery et al. | 128/207.14 |
| 4,501,029 | 2/1985 | McMinn | 128/334 R |
| 4,583,969 | 4/1986 | Mortensen | 623/9 |
| 4,617,932 | 10/1986 | Kornberg | 623/1 |

Primary Examiner—Richard J. Apley
Assistant Examiner—David J. Isabella
Attorney, Agent, or Firm—Kane, Dalsimer, Sullivan, Kurucz, Levy Eisele and Richard

[57] ABSTRACT

An improved tracheobronchial stent has a T-Y shape with specific curves at the T and the Y intersections to minimize insult to the tracheal and bronchial tissues when used as a long-term prosthetic device.

7 Claims, 4 Drawing Sheets

TRACHEOBRONCHIAL STENT

BACKGROUND OF THE INVENTION

1. Field of the Invention

The invention relates to prosthetic devices for use in mammals, including humans, and more particularly relates to a T-Y shaped tracheobronchial stent.

2. Brief Description of the Prior Art

Prosthetic stents have been employed following surgical reconstruction of the cervical portion of the trachea and the surgical correction of tracheal and subglottic stenosis as well as for maintaining an otherwise obstructed tracheobronchial airway. Representative of prior art descriptions are those found in U.S. Pat. No. 3,721,233 and in the article by Westaby et al., J. of Thoracic and Cardiovascular Suggery, Vol. 83, pps 414–417 (1982).

SUMMARY OF THE INVENTION

The invention comprises in a tracheobronchial stent, which comprises;

a flexible tube of a synthetic, polymeric resin, including
  (A) an open tracheal end;
  (B) a bifurcated bronchial end comprising
    (i) a left bronchial branch extending along a substantially straight axial line and having an end which is continuous and integral with the tracheal zone described hereinbelow, and a terminal, open end distal to said tracheal zone; and
    (ii) a right bronchial branch having an end which is continuous and integral with the tracheal zone described hereinbelow, and a terminal, open end distal to said tracheal zone;
  (C) a tube wall extending continuously from the tracheal end to each of the left and right bronchial branch terminal ends, and defining a continuous lumen providing open fluid communication between the open tracheal end and the open terminal ends, said tube wall having
    (i) a tracheal zone extending from the tracheal end to the bifurcated branched end, along a substantially straight axial line;
    (ii) an opening through the wall in the tracheal zone; and
    (iii) a bronchial zone which comprises the left and the right branches together; and
  (D) a tracheotomy tube mounted on the wall of the flexible tube and having
    (i) a first open end integrally joined to the flexible tube wall in the tracheal zone so as to enclose the opening in the tracheal zone;
    (ii) a second open end distal to the flexible tube juncture; and
    (iii) a tracheotomy tube wall between the first and second open ends and defining a tracheotomy tube lumen providing open fluid communication between the second open end and the lumen of the flexible tube through the opening in the tracheal zone of the flexible tube wall;

the improvement, which comprises;

an angle of from 40° to 60° formed by the intersection of the axial line of the flexible tube and the axial line of the left bronchial branch as measured on the left bronchial branch side of the intersection;

an angle of from 5° to 25° formed by a second intersection of the axial line of the flexible tube with the axial line of the right bronchial branch as measured on the right bronchial branch side of the second intersection a ratio of the outer diameter of the tracheal zone to the outer diameter of the left bronchial branch of 1.0:0.4–0.6;

a ratio of the outer diameter of the tracheal zone to the outer diameter of the right bronchial branch of 1.0: 0.4–0.6; and an arc between the left and the right bronchial branches, said arc being part of a circle having a radius of from 200 to 10.0 mm.

The stent of the invention provides internal support for the trachea following surgery, promotes healing with minimal encouragement for the growth of scar tissue, maximizes support surface contact and reduces isolated pressure points as a cause for the stimulation of recurrent stenosis.

The stent of the invention is also useful in the management of an airway obstruction in the trachea, bronchial carina and main bronchi, such as may be caused by tumor, scar tissue and like conditions.

An advantage of the stent of the invention is found in its compatibility with the mammalian physiology, enabling it to be left in the tracheobronchial zone for extended periods of time without adverse effect on the host mammal.

DETAILED DESCRIPTION OF THE PREFERRED EMBODIMENTS OF THE INVENTION

Those skilled in the art will gain an appreciation of the invention from the following description of the preferred embodiments of the invention, when read in conjuction with a viewing of the accompanying drawings of FIGS. 1–6, inclusive.

Figure 1:
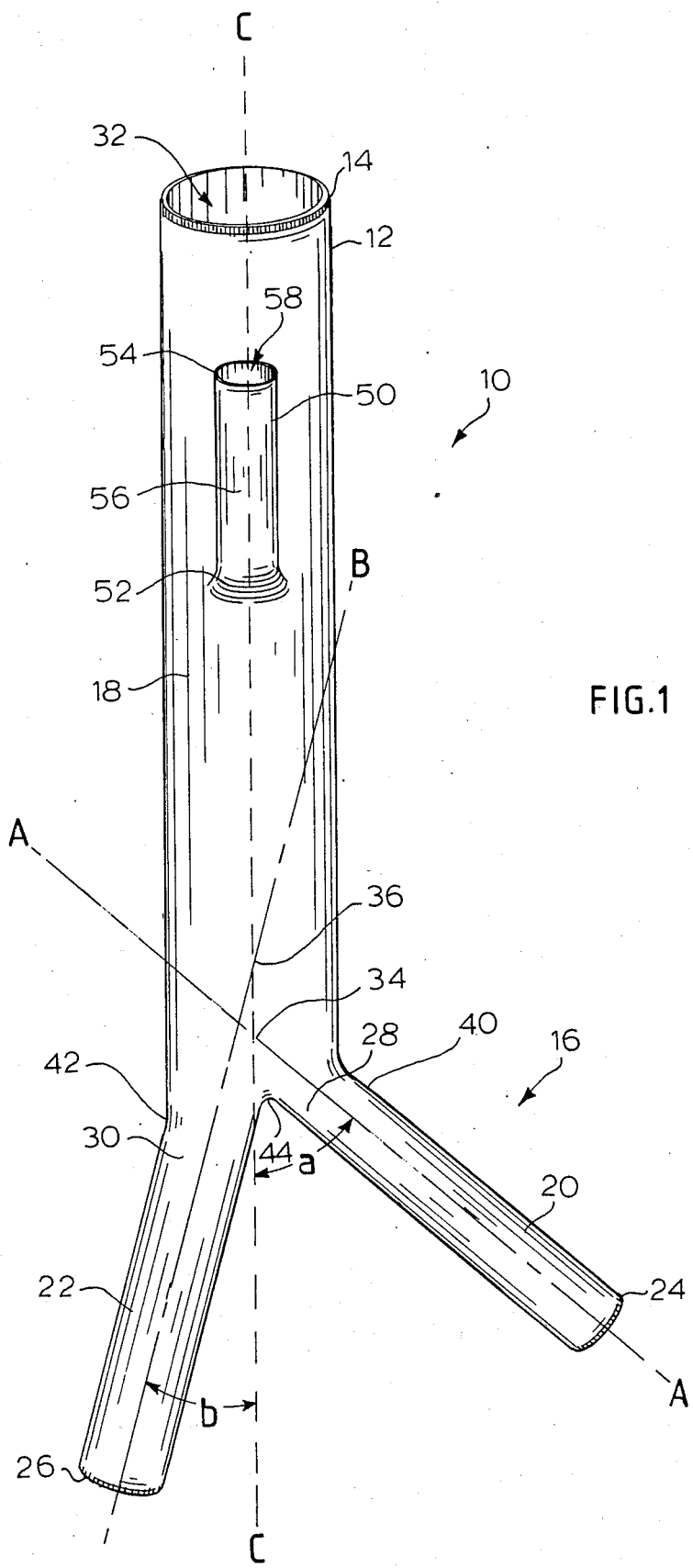
FIG. 1 is a front view of an embodiment stent of the invention.

FIG. 1 is a front view of an embodiment stent 10 of the invention. The stent 10 comprises a flexible, resilient tube 12 fabricated from a synthetic, polymeric resin which is medically acceptable in a prosthetic device for implantation in a mammalian trachea. Preferably, the tube 12 is fabricated from a resiliently yieldable resin such as a polysilicone rubber composition. Preferred is a medical grade (Food and Drug Administration approved) silicone rubber.

A silicone rubber is herein defined generally as a cross-linked silicone elastomer of the type vulcanized at room temperature (RTV) or at elevated temperatures (HTV). Dimethyl siloxanediol with silicone resin or alkyl silicate as cross-linking agents are typically used. Typically, fillers such as silica, calcium carbonate, titanium oxide and the like are normally added to the polymer formulation, usually by the manufacturer of the silicone polymer, as the filler materials provide degrees of rigidity and softness.

One example of a silicone rubber which may be used in the stent of the invention is Dow Corning 3110 RTV silicone rubber. This material can be cross-linked at room temperature with Dow Corning RTV catalyst No. 4. Other silicone rubber resins are well known and available commercially and techniques of molding them are well known to the artisan.

The tube 12 has an open tracheal end 14 which is feathered outwardly to facilitate its use in the inner aspect of a trachea, at a point within the trachea just below the cricoid cartilage. At the opposite end of tube 12 is a bifurcated bronchial end 16, which is continuous and integral with a tracheal zone 18 of the tube 12. The bronchial end 16 consists of a left bronchial branch 20 and a right bronchial branch 22 which in use are inserted in the left bronchus and the right bronchus, respectively, of the mammalian bronchi. Thus, the branches 20, 22 constitute a bronchial zone of the tube 12 which is a unitary, continuous tube from end 14 to the terminal ends 24, 26 of the respective bronchial branches 20, 22. The terminal ends 24, 26 of branches 20, 22 may also be feathered outwardly in the same manner as is the tracheal end 14, to facilitate installation within the bronchi of a mammal. The upper end 30 of right branch 22 is continuous with the tracheal zone 18 of tube 12. The upper end 28 of left bronchial branch 20 is continuous with and arises from the right bronchial branch 22 at a point adjacent to the juncture of the branch 22 with the tracheal zone 18. The branches 20, 22 at ends 28, 30 form the arms of an inverted "Y" with the apex of the joined arms at point 44 which during use of the stent 10 bridges and is supported by the bronchial carina and in turn supports the bronchial carina. The branches 20, 22 extend from ends 28, 30, respectively to ends 24, 26, respectively along a substantially straight axial line A—A and a line B—B, respectively, as shown in the FIG. 1. The axial lines A—A and B—B intersect with an axial line C—C which is substantially straight and centered on the tracheal zone 18 of the tube 12. The tube 12 comprises then, a tube wall extending continuously from the tracheal end 14 to each of the terminal ends 24, 26. The tube 12 wall defines a continuous lumen 32 which provides open fluid communication between the open tracheal end 14 and the open terminal ends 24, 26. The wall of tube 12 may be of a homogeneous, synthetic polymeric resin material as described above or it may consist of two different polymer materials. For example, the tracheal zone 18 is preferably fabricated from a relatively hard, self-supporting but flexible silicone rubber having an indentation hardness of from 45 to 70 (Shore A durometer). The bronchial zone on the other hand is preferably of a softer, less rigid flexible polymer and preferably has an indentation hardness of from 35 to about 55 (Shore A durometer). Techniques for fabricating unitary articles from diverse synthetic polymeric resins of different softness are well-known to those skilled in the art and details need not be recited herein. This difference in hardness between the areas or zones of the stent 10 optimize the stent 10 to meet different physical specifications to maintain a prosthetic function in two diverse tissues, i.e., the tracheal tissues and the bronchial tissues, and facilitates insertion of the stent 10 into a mammal.

In fabricating the tube 12, the tracheal zone 18 is preferably substantially straight to the point of bifurcation at bronchial zone 16. The bifurcation is such that the axial line A—A for the left bronchial branch intersects with the axial line C—C of the tracheal zone (Point 34) at an angle "a" within the range of from 40° to 60° preferably 45° to 55°; most preferably about 50°. The axial line B—B of the right bronchial branch advantageously intersects with the axial line C—C (Point 36) at an angle "b" within the range of from 5° to 25°; preferably about 10° to 20°, most advantageously about 15°. When the angles of intersection of lines A—A and B—B with line C—C are within the preferred ranges, the curve at Point 40 on the exterior of tube 12 is an arc forming part of a circle having a radius of from 9 to 20 millimeters, preferably about 14 millimeters. The curve formed on the exterior of tube 12 at Point 42 is advantageously an arc forming part of a circle having a radius of from 20 to 30 millimeters, preferably about 25 millimeters. The curves described at points 40, 42 provide a smooth transition between the tracheal zone 18 and the bronchial zone 16 to minimize pressure points against mammalian tissue when the stent 10 is placed in use. The point 44 between branches 20, 22 on the exterior of tube 12 is advantageously on an arc forming part of a circle having a radius of from 2 to 10 millimeters, preferably about 5 millimeters and serves also to minimize pressure points upon adjacent tissues by providing a smooth transition between the branches 20, 22.

The internal radii of the tube 12 at points 40, 42 on the inner wall defining in part lumen 32 mirrors the outer arc and is equal in curvature to facilitate suctioning and cleaning of the lumen 32 when needed.

The above described angles and curvatures are necessary to the stent 10 of the invention. When positioned correctly within the trachea and bronchi of the mammal, a stent 10 of the invention having the necessary angles and curvatures is fully supported and supports fully the trachea, bronchial carina and upper bronchi so that there is minimal movement between the stent and the anatomical sites supported. There is therefore a minimal irritation of the tissue at these sites with less potential for irritated pressure points to develop with consequent stimulation of scar tissue development. In contrast, a stent having angles and curvatures outside of the ranges specified above is prone to promote the undesired irritation of affected tissue. The wall thickness of the tube 12 may be varied over a considerable range, but is preferably within the range of from about 0.90 to about 2.0 millimeters, most preferably circa 1.5 millimeters. It will be seen in FIG. 1 that the left bronchial branch 20 arises out of the right bronchial branch 22 in such a way that the point 44 is offset from the axial line C—C, towards left branch 20. The offset distance is advantageously equal to from 10 to 15 percent of the diameter of the tube 12 in the tracheal zone 18. This offset is essential to the elimination of a source of pressure point irritation of the bronchial carina when the stent 10 is placed in use. The outside diameter of the tube 12 may be varied to meet specific requirements in the tracheal-bronchial dimensions of the mammal to receive of the stent 10. The tube 12 must fit snugly within the trachea and left and right bronchus to provide anatomical support in those anatomical areas. By way of example, the outside diameter of the tracheal zone of tube 12 may range from 8 to about 16 millimeters, depending on the tracheal lumen diameter of the mammal receiving the prosthesis. Similarly, the length of the tracheal zone 18 of the tube 12 may range in accordance with the anatomical requirements of the mammal. A length adjustment may be made by trimming end 14. The outer diameter of the left branch 20 is preferably within the range of from about 3.0 to about 10.0 millimeters and the diameter of the right branch 22 is preferably within the range of from about 3.0 to about 10.0 millimeters. The ratio of the tube 12 diameter to the diameter of the branches 20, 22 is a departure from the prior art. Again, the selection of a specific diameter is made to meet a specific anatomical requirement. Advantageously, the ratio of the outer diameter of the tracheal zone 18 immediately above the bronchial zone 16, to the diameter of the left branch 20 is within the range of from 1.0:0.4 to 0.6 and the ratio to the right branch 22 is within the range of from 1.0:0.4 to 0.6. This ratio is a departure from the prior art. The advantage resides in enhanced support for the bronchi with less potential for creation of pressure points on the bronchial tissue. The length of the branches 20, 24 is advantageously within the range of from 2.0 to 5.0 cm., preferably about 4.0 cm. and may be adjusted for a given mammal by trimming the ends 24, 26 to an exact dimension.

Mounted on a point within the tracheal zone 18 and structurally integral with tube 12 is a tracheotomy tube 50. The tracheotomy tube 50 has a first open end 52 which is integrally joined to the flexible tube 12 wall in the tracheal zone 18 so as to close an opening in the tracheal zone (opening not seen in FIG. 1; see FIG. 3). A second open end 54 distal to the flexible tube 12 juncture is open to the atmosphere. A tracheotomy tube wall 56 between the ends 52, 54 defines a tracheotomy tube lumen 58 which provides open fluid communication between the open end 54 and the lumen 32 of the flexible tube 12, through the opening in the tracheal zone 18 of the flexible tube 12 wall. The opening 60 in tracheal zone 18 is seen best in FIG. 3. As will be appreciate, the tracheotomy tube 50 is of a lesser diameter than the tube 12 in tracheal zone 18. The length of tube 50 may be of a sufficient dimension to protrude through an incision in the mammal's trachea and overlying tissues, so that communication of the stent 10 lumen 32 to the atmosphere is provided.

Figure 2:
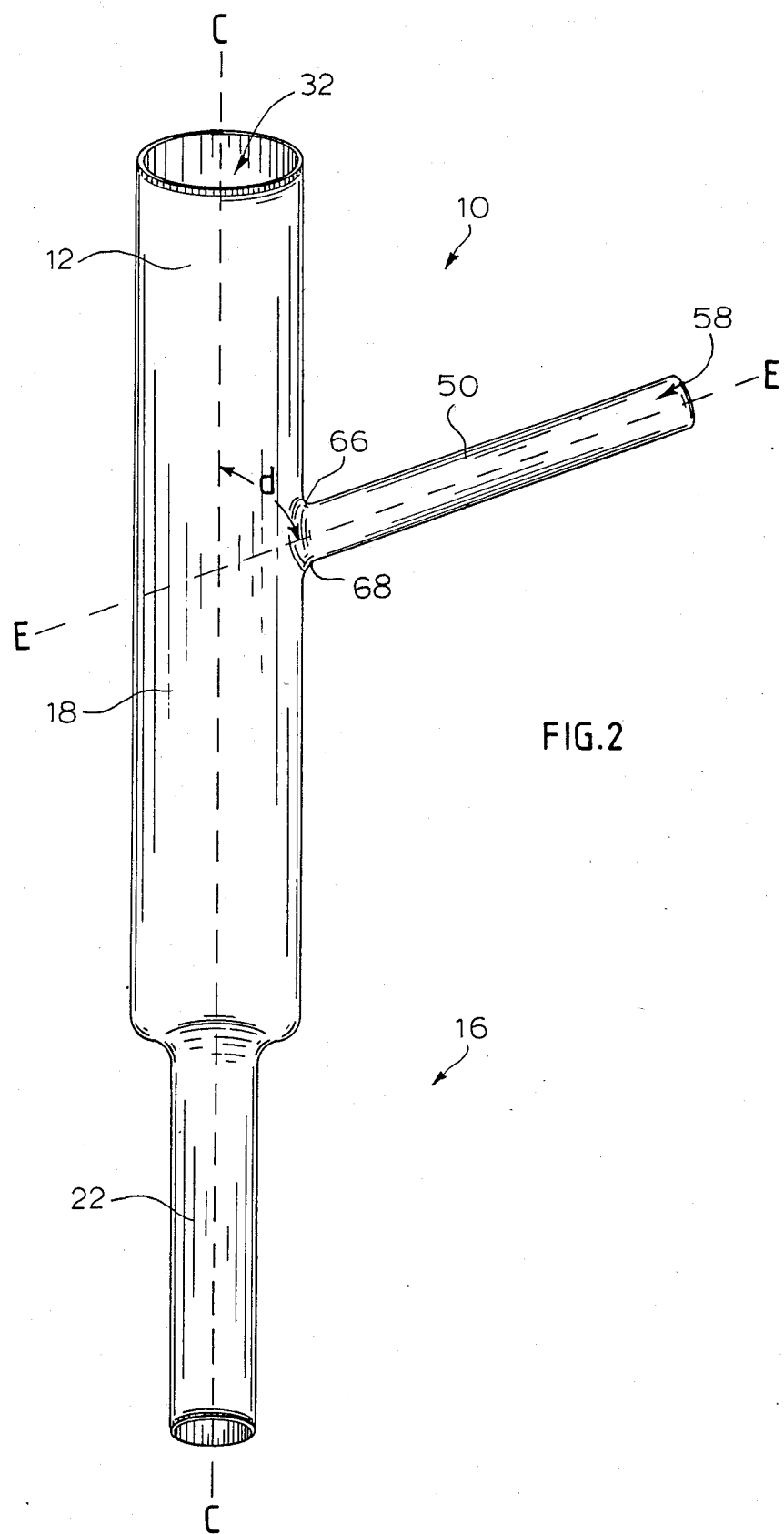
FIG. 2 is a side view of the stent shown in FIG. 1.

As shown in FIG. 2, the juncture between the tracheotomy tube 50 and the tracheal zone 18 of tube 12 provides a smooth rounded shoulder to minimize stenosis of the tracheal wall contacting the stent 10 at this site and to provide maximum support of the stoma at this site. The tracheotomy tube 50 is substantially straight and extends along a substantially straight axial line E—E. This axial line E—E intersects with the axial line C—C of tube 12 at an angle "d" of from about 10° to 30°; preferably 15° to 25° and most preferably around 20° as measured in the direction of end 14 of the tracheotomy tube 50. This specified angle range is a departure from the prior art and facilitates insertion of the stent 10 into the trachea and enable one to obtain a better fit. The tracheotomy tube 50 is preferably fabricated from a relatively rigid polymer in comparison to the tube 12. Advantageously, the tracheotomy tube 50 will be fabricated from a synthetic, polymeric resin having a relative stiffness found in conventional tracheotomy tubes. The rounded shoulder at Point 66 is preferably an arc forming part of a circle with a radius of from 3 to 8 millimeters, preferably around 5 millimeters. At an opposing point on tube 50, the Point 68 is preferably an arc forming part of a circle having a radius of from about 15 to about 25 millimeters; preferably about 20 millimeters. The region on the circumference of tube 50 between points 66 and 68 advantageously are a compromise in the above-described arcs for a gentle and gradual gradation of shoulder between the two points 66, 68.

The radius of the curve at the juncture of the tracheotomy tube 50 with the wall of the tube 12 is critical to avoid anterior tracheal stenosis and a recurrent stenosis. The configuration obtained by the specified arc supports the posterior surface of the tracheotomy orifice and discourages the development of scar tissue inward from the inferior margin of the incised tracheal wall at the tracheotomy opening. The curvatures of the internal surfaces of the tube 12 defining the lumen 32 of the tube 12 and the lumen 58 of tracheotomy tube 50 at the juncture of tubes 12, 50 mirror the curvatures of the external surfaces at the juncture (points 66,68 and the intervening shoulder) so that the interior of the combined tubes 12, 50 is also a smooth transition between the tubes 12, 50. This smooth curvature facilitates suctioning and cleaning of the lumens 32, 58, if necessary.

The procedure for installing or implanting the stent 10 in a mammal and for its maintenance and operation will be obvious to the skilled artisan and may include the procedures described by Westaby et al., supra., incorporated herein by reference thereto.

Figure 3:
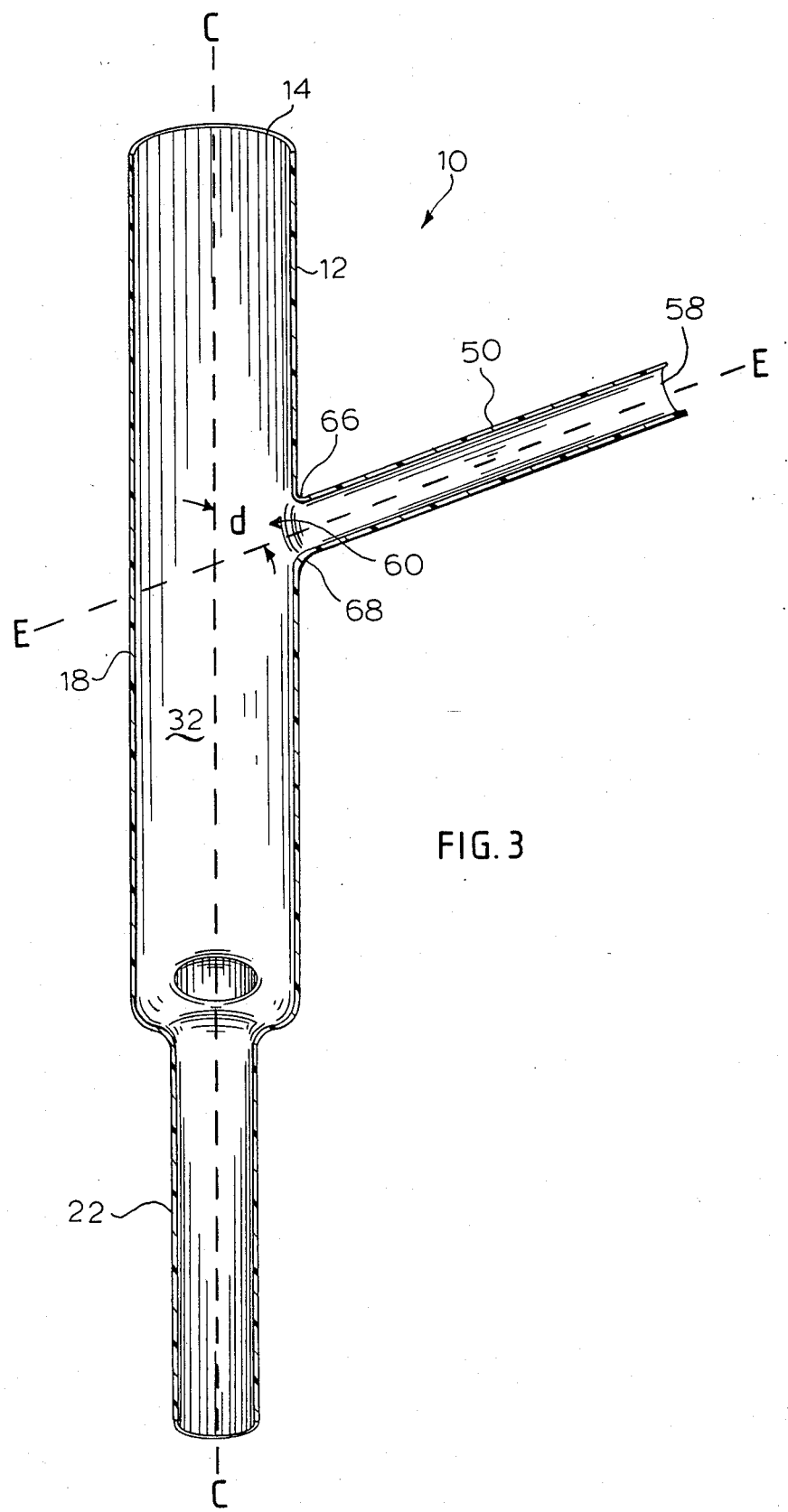
FIG. 3 is a cross-sectional (in part) view of the stent as shown in FIG. 2.

FIG. 3 is a cross-sectional (in part) view of the stent 10 as shown in FIG. 2 and provides additional details of the stent 10 as previously described above.

Removable closures for tracheotomy tubes which are readily emplaced and removed by the patient or nursing staff have been a problem in the art. Too often, the closures are difficult to remove quickly and without causing momentary panic on the part of the patient. The present invention includes a new closure member which overcomes this problem of the art.

Figure 4:
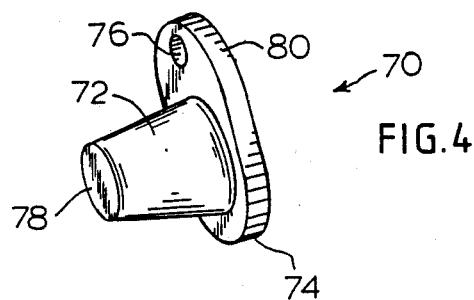
FIG. 4 is a view-in-perspective of an embodiment closure for the tracheotomy tube component portion of the embodiment stent shown in FIGS. 1–3.
Figure 5:
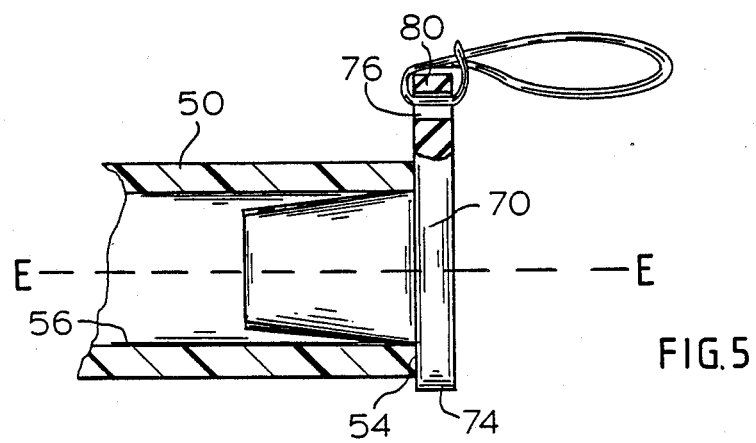
FIG. 5 is a view in cross-section of the embodiment closure of FIG. 4, emplaced in the open end of a tracheotomy tube.
Figure 6:
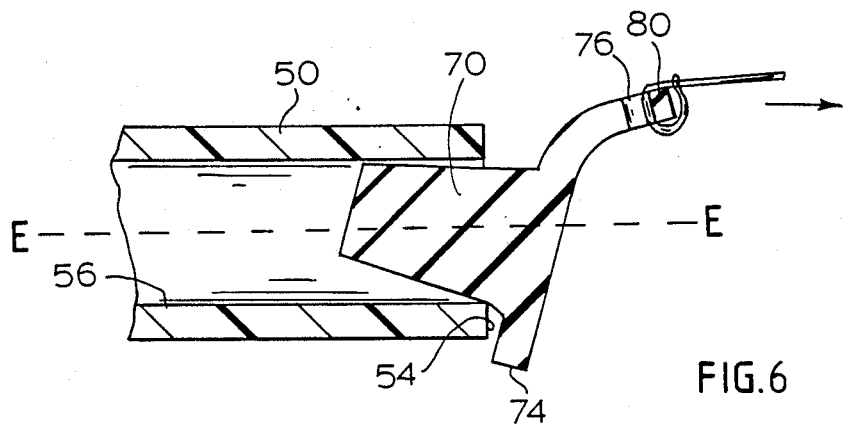
FIG. 6 is a view as in FIG. 5, in which the closure is in an initial stage of removal.

FIG. 4 is a view in perspective of an embodiment closure 70 for the tracheotomy tube 50 component portion of the embodiment stent 10 shown in FIGS. 1-3. The closure 70 is a solid cylindrical plug 72 having an outer flange 74 disposed about the periphery of one end of plug 72. The peripheral flange 74 may have an aperture 76 therein for securing the plug 70 with a cord or thong attachment to minimize loss when the closure 70 is removed from closing the tube 50. The plug 72 tapers from a maximum diameter at the flange 74 end to a minimum diameter at end 78. In addition, the end 78 may be outwardly feathered to facilitate insertion in tube 50. The degree of taper is preferably within the range of from 1° to 5°; preferably about 3°. Preferably the length of plug 72 is within the range of from about 5 to about 15 millimeters. The material from which plug 70 is fabricated is preferably a synthetic polymeric resin having a smooth surface finish. Representative of such resins are polyethylene, polypropylene, polycarbonate, polysilicone and the like. The closure 70 may be fabricated in a size and configuration to sealingly nest within open end 54 of the tracheotomy tube 50 component of stent 10 providing a fluid seal as shown in FIG. 5. The closure 70 is removably mounted within end 54 of tube 50 when it is desired to close off the atmosphere from communication with lumen 32 of stent 10 via tube 50. For removal, one may grasp the flange 74 and exert an outward and biased pressure on the closure member 70, whereby it is misaligned with the axial line path E—E of opening 54, thereby breaking surface contact between plug 72 and the inner wall 56 of the tracheotomy tube 50; see FIG. 5. This misalignment of the closure member 70 within opening 54 facilitates its removal.

In the preferred embodiment closure 70, a portion of the flange 74 is enlarged (to give an eccentric shape)

providing a finger gripping zone 80, to facilitate removal of the closure 70.

What is claimed is:

1. In a tracheobronchial stent, which comprises;
a flexible tube of a synthetic, polymeric resin, including
  (A) an open tracheal end;
  (B) a bifurcated bronchial end comprising
    (i) a left bronchial branch extending along a substantially straight axial line and having an end and a terminal, open end and
    (ii) a right bronchial branch having an end and a terminal, open end
  (C) a tube wall extending continuously from the tracheal end to each of the left and right bronchial branch terminal ends, and defining a continuous lumen providing open fluid communication between the open tracheal end and the open terminal ends, said tube wall having
    (i) a tracheal zone extending from the tracheal end to the bifurcated branched end, along a substantially straight axial line;
    (ii) an opening through the wall in the tracheal zone; and
    (iii) a bronchial zone which comprises the left and the right branches together; and
  (D) a tracheotomy tube mounted on the wall of the flexible tube and having
    (i) a first open end integrally joined to the flexible tube wall in the tracheal zone so as to enclose the opening in the tracheal zone;
    (ii) a second open end distal to the flexible tube juncture; and
    (iii) a tracheotomy tube wall between the first and second open ends and defining a tracheotomy tube lumen providing open fluid communication between the second open end and the lumen of the flexible tube through the opening in the tracheal zone of the flexible tube wall;
the improvement, which comprises;
  (E) an angle of from 40° to 60° formed by the intersection of the axial line of the flexible tube and the axial line of the left bronchial branch as measured on the left bronchial branch side of the intersection;
  (F) an angle of from 5° to 25° formed by the intersection of the axial line of the flexible tube and the axial line of the right bronchial branch as measured on the right bronchial branch side of the intersection;
  (G) a ratio of the outer diameter of the tracheal zone to the outer diameter of the left bronchial branch of 1.0:0.4–0.6;
  (H) a ratio of the outer diameter of the tracheal zone to the outer diameter of the right bronchial branch of 1.0:0.4–0.6; and
  (I) an arc between the left and the right bronchial branches, said arc being part of a circle having a radius of from 2 to 10 mm.

2. The stent of claim 1 wherein the resin is a silicone rubber.

3. The stent of claim 2 wherein the silicone rubber in the tracheal zone has an indentation hardness of from 45 to 70 Shore A durometer and the silicone rubber in the bronchial zone has an indentation hardness of from 35 to 55 Shore A durometer.

4. The stent of claim 1 wherein the axial line of the flexible tube is a centerline of the flexible tube and the left bronchial branch is offset from the centerline by a distance equal to from 10 to 15 percent of the diameter of the flexible tube in the tracheal zone.

5. The stent of claim 1 wherein the angle (E) is 50°; the angle (F) is 5°; the ratio (G) is from 1.0:0.5; the ratio (H) is from 1.0:0.5; and the radius (I) is 5 mm.

6. The stent of claim 1 wherein the tracheotomy tube joins the flexible tube at an angle of from 10° to 30°.

7. The stent of claim 1 which further comprises a removable closure for the open end of the tracheotomy tube.

* * * * *

UNITED STATES PATENT AND TRADEMARK OFFICE
CERTIFICATE OF CORRECTION

PATENT NO.   :   4,795,465
DATED        :   January 3, 1989
INVENTOR(S)  :   Lewis H. Marten It is certified that error appears in the above—identified patent and that said Letters Patent is hereby corrected as shown below:

Col. 1, line 17; "Suggery" should read -- Surgery -- .

Col. 2, line 11; "200" should read -- 2.0 -- .

Col. 5, lines 35-36; "appreciate" should read -- appreciated --.

Signed and Sealed this

Eleventh Day of July, 1989

Attest:

DONALD J. QUIGG

Attesting Officer

Commissioner of Patents and Trademarks